US011291191B2

(12) United States Patent
Meissner et al.

(10) Patent No.: US 11,291,191 B2
(45) Date of Patent: Apr. 5, 2022

(54) METHOD AND DEVICE FOR TREATING POULTRY EGGS USING ELECTRON BEAMS TO STERILISE THE CALCAREOUS SHELL

(71) Applicant: COMET AG, Flamatt (CH)

(72) Inventors: Sven Meissner, Brand-Erbisdorf (DE); Björn Fischer, Limbach-Oberfohna (DE)

(73) Assignee: Skan Stein AG, Stein (CH)

( * ) Notice: Subject to any disclaimer, the term of this patent is extended or adjusted under 35 U.S.C. 154(b) by 247 days.

(21) Appl. No.: 16/314,353

(22) PCT Filed: Jun. 28, 2017

(86) PCT No.: PCT/EP2017/065951
§ 371 (c)(1),
(2) Date: Jan. 24, 2019

(87) PCT Pub. No.: WO2018/002112
PCT Pub. Date: Jan. 4, 2018

(65) Prior Publication Data
US 2019/0200579 A1    Jul. 4, 2019

(30) Foreign Application Priority Data

Jul. 1, 2016   (DE) .......................... 102016008291.7

(51) Int. Cl.
*A01K 43/00*        (2006.01)
*A23B 5/015*        (2006.01)
(Continued)

(52) U.S. Cl.
CPC ............ *A01K 43/005* (2013.01); *A01K 43/00* (2013.01); *A01K 45/007* (2013.01); *A23B 5/015* (2013.01);
(Continued)

(58) Field of Classification Search
CPC .... A01K 43/005; A01K 43/00; A01K 45/007; G21K 5/10; G21K 5/08; G21K 5/04;
(Continued)

(56) References Cited

U.S. PATENT DOCUMENTS 2,456,909 A * 12/1948 Brasch .................... A23L 3/263
                                                              422/22
2,806,797 A *  9/1957 Brasch .................... A23L 3/263
                                                              426/240
(Continued)

OTHER PUBLICATIONS

PCT EP2017065951, Search Report, English translation, dated Oct. 12, 2017 (Year: 2017).*
(Continued)

*Primary Examiner* — David A Vanore
(74) *Attorney, Agent, or Firm* — Blank Rome LLP (57) ABSTRACT

A method and a device for treating poultry eggs with an electron beam bundle to sterilize the calcareous shell are disclosed. The method includes moving at least one egg through the beam path of an electron beam source; irradiating the eggs, whereby the calcareous shell is irradiated with a varying dose; and either carrying out an irradiation encompassing all regions of the calcareous shell of the egg by employing the electron beam bundle, whereby an element is inserted into the path of the electron beam bundle; carrying out an irradiation of a rolling/rolled egg by employing the electron beam source in the path of the electron beam bundle; or carrying out an irradiation of the held eggs by employing the electron beam source in the electron beam bundle path at a zero degree position of one side in a device arranged upstream of a turning device.

13 Claims, 8 Drawing Sheets

(51) Int. Cl.

| | |
|---|---|
| *A01K 45/00* | (2006.01) |
| *G21K 5/10* | (2006.01) |
| *G21K 5/08* | (2006.01) |
| *A23L 3/26* | (2006.01) |
| *A23L 3/32* | (2006.01) |
| *G21K 5/04* | (2006.01) |
| *A23L 3/005* | (2006.01) |
| *A61L 2/08* | (2006.01) |

(52) U.S. Cl.
CPC ............... *A23L 3/005* (2013.01); *A23L 3/26* (2013.01); *A23L 3/32* (2013.01); *A61L 2/087* (2013.01); *G21K 5/04* (2013.01); *G21K 5/08* (2013.01); *G21K 5/10* (2013.01)

(58) Field of Classification Search
CPC ... A23L 3/26; A23L 3/32; A23L 3/005; A23B 5/015; A61L 2/087
See application file for complete search history.

(56) References Cited

U.S. PATENT DOCUMENTS

| | | | | |
|---|---|---|---|---|
| 2,807,551 | A * | 9/1957 | Brasch | A23L 3/263 |
| | | | | 426/234 |
| 2,987,182 | A * | 6/1961 | Ator | G01N 33/085 |
| | | | | 209/511 |
| 4,246,295 | A * | 1/1981 | Crihan | B27K 3/08 |
| | | | | 422/22 |
| 5,700,504 | A * | 12/1997 | Hale, Jr. | A23B 5/015 |
| | | | | 426/240 |
| 5,939,720 | A * | 8/1999 | Todokoro | H01J 37/244 |
| | | | | 250/310 |
| 6,096,379 | A * | 8/2000 | Eckhoff | A23B 4/015 |
| | | | | 426/237 |
| 2003/0127593 | A1* | 7/2003 | Shinada | H01J 37/29 |
| | | | | 250/310 |
| 2006/0243906 | A1* | 11/2006 | Fukada | H01J 37/28 |
| | | | | 250/307 |
| 2008/0073549 | A1* | 3/2008 | Avnery | G21K 5/04 |
| | | | | 250/397 |
| 2008/0121803 | A1* | 5/2008 | Shojo | H01J 37/244 |
| | | | | 250/307 |
| 2009/0092708 | A1* | 4/2009 | Alvarado | A23B 5/06 |
| | | | | 426/62 |
| 2010/0130805 | A1* | 5/2010 | Roeder | C02F 1/305 |
| | | | | 588/305 |
| 2015/0056095 | A1* | 2/2015 | Gorzen | A61L 2/087 |
| | | | | 422/23 |
| 2018/0196024 | A1* | 7/2018 | Hurlin | A01K 45/005 |
| 2020/0196646 | A1* | 6/2020 | Gildersleeve, III | A47J 29/06 |

OTHER PUBLICATIONS

S. Cadirci: *Disinfection of hatching eggs by formaldehyde fumigation—a review*, Arch. Geflügelk. 73 (2), pp. 1 16.123, 2009.

Trenner, Profe: *Die konsequente Anwendung der Dampfdesinfektion zur Unterbrechung von Infektionsketten*, 21. Kongress der Deutschen Veterinärmedizinschen Gesellschaft e.V., Bad Nauheim, Mar. 21 to 24, 1995, current research, part 2, pp. 461-465.

TRGS 513: *Begasung mit Ethylendioxid and Formaldehyd in Sterilisations- and Desinfektionsanlagen*, Jun. 1996, pp. 1-4.

\* cited by examiner

METHOD AND DEVICE FOR TREATING POULTRY EGGS USING ELECTRON BEAMS TO STERILISE THE CALCAREOUS SHELL

This application is a U.S. national stage application based on International Application No. PCT/EP2017/065951, filed Jun. 28, 2017, which claims priority to German Patent Application No. 102016008291.7, filed Jul. 1, 2016, both of which are herein incorporated by reference in their entirety.

BACKGROUND OF THE INVENTION

The invention relates to a method and a device for treatment of poultry eggs using electron beams for a sterilization of the calcareous shell. Poultry eggs can be eggs for human consumption, industrial eggs and also hatching eggs. For example, in industrial poultry production as well as in the field of production of SPF (Specific Pathogen Free) eggs for the vaccine industry, according to the publications S. Cadirci: *Disinfection of hatching eggs by formaldehyde fumigation—a review*, Arch. Geflügelk. 73 (2), pp. 116.123, 2009, ISSB 0003-9098, publisher Eugen Ulmer, Stuttgart; Trenner, Profe: *Die konsequente Anwendung der Dampfdesinfektion zur Unterbrechung von Infektionsketten*, 21. Kongress der Deutschen Veterinarmedizinschen Gesellschaft e.V., Bad Nauheim, 21 to 24 Mar. 1995, current research, part 2, pp. 461-465; TRGS 513: *Begasung mit Ethylendioxid and Formaldehyd in Sterilisations—and Desinfektionsanlagen*, June 1996 issue (BArbBl. Heft 6/1996, s. 53-58) last amended and supplemented in February 2000 (BArbBl. issue 2/2000, p. 80), hatching eggs are sterilized before the beginning of the hatching process in order to prevent an uncontrolled spread of microbes during the hatching connected with hatching losses as well as a stressing of the hatching chick.

The most widespread method at the present time for surface treatment of hatching eggs for germ reduction is the fumigation with formaldehyde. For this purpose, for example, paraformaldehyde powder is heated in the so-called dry method. The resulting gas is distributed in the gas chamber in such a way that as homogenous as possible a concentration per cubic meter ambient air arises and has an effect upon the hatching eggs for about 20 minutes. Following the treatment the chamber is ventilated to the outside atmosphere. Owing to its toxic and carcinogenic effect on the environment, the method is judged extremely critically. Moreover an overdose can lead to a significant impairment of successful hatching. Another great disadvantage of the formaldehyde fumigation is the limitation to a purely surface treatment. Microbes which are located far inside the microporous calcareous shell cannot be killed.

Alternative approaches to hatching egg disinfection, such as treatment using peracetic acid or various fruit acids, have not gained acceptance so far. Complex physical treatment methods such as ozone or plasma treatment have failed so far because of the practical feasibility or respectively cost-effectiveness.

The physical method of electron beam sterilization is used at the present time in the area of foodstuffs above all for treatment of outer packaging, poultry meat or raw egg mass. The aim, on the one hand, is the inactivation of poultry pathogens as well as the modification of certain foodstuff components (albumen): To achieve as great an effective depth as possible, the operation is carried out with comparatively high acceleration voltages in the MeV range.

BRIEF SUMMARY OF THE INVENTION

The invention thus has as its object to indicate a method and device for treatment of poultry eggs with electron beams for a sterilization of the calcareous shell which is suitably designed in such a way that a reduction is possible of the electron dose gradient brought about by the different distances of the hatching eggs to the electron beam source. Furthermore the electron irradiation of the egg should take place uniformly over the entire egg.

The object is achieved through the features of claims 1 and 3, 6, 8.

The method for treatment of poultry eggs with electron beams for a sterilization of the calcareous shell has the following steps:

moving at least one egg through the beam path of an electron beam source, irradiating the eggs using an electron beam bundle from the electron beam source, whereby the calcareous shell is irradiated with a varying dose, whereby according to the characterizing portion of claim 1 the following steps are carried out:

carrying out an irradiation encompassing all regions of the calcareous shell of the egg using the electron beam bundle whereby an element is inserted into the path of the electron beam bundle to distribute the irradiation over all regions of the calcareous shell, whereby owing to the dose being set within a predefined target dose range, the calcareous shell is comprehensively irradiated, or carrying out an irradiation by means of the electron beam source of a rolling egg in the path of the electron beam bundle, whereby owing to the respective predefined rotational angle of the rolled egg the calcareous shell is irradiated comprehensively in a uniform way, or carrying out an irradiation of the held eggs in a zero degree position of the one side in a device arranged upstream of the turning device, turning of the held eggs in a turned angular degree position with respect to the zero degree position, e.g. in a 180 degree position, by the turning device and carrying out a another irradiation of the reached side of the egg by means of a device arranged downstream of the turning device, which downstream device is constructed in an analogous way to the device arranged upstream, whereby owing to the turned egg the calcareous shell is comprehensively irradiated. Coming under consideration as poultry eggs to be treated with electron beams can be eggs for human consumption, industrial eggs and also hatching eggs as well as eggs for other purposes and industrial fields.

In the method substantially the following method steps can be carried out for the treatment of eggs to be accomplished using electrons:

sensing A the height of the egg (42, 43), moving B into the shielded area through a gate (45), treatment C with corresponding height correction unit (8), moving D out of the shielded area through a gate (46) and optional recontamination E of the eggs (42, 43) and transfer of the egg (42, 43) for subsequent process steps.

A first device for treatment of poultry eggs with electron beams for a sterilization of the calcareous shell, using one of the aforementioned methods at least comprises:

a transport system with at least one egg, an electron beam source for emission of an electron beam bundle, through whose path the eggs are led in a way treated with electrons in a treatment area, whereby according to the characterizing portion of claim 3<sic. 5>
for setting the dose of the electrons hitting the calcareous shell in a target dose range, an element is disposed between the electron beam source and the supported egg/eggs so that in a predefined target dose range a reduced distribution, encompassing the egg, of the dose of the electrons is achieved for irradiation of the calcareous shell of the eggs.

The element for setting the dose can be an electron baffle. The element for setting the dose can be a steel sheet, a rod, a rhombus, a circle of aluminum or a rhombus with a gap.

The first device can have the following units and lines:
the central control unit,
an electron beam generator/an electron beam source,
a shielding device around the treatment unit,
the electron baffle,
a transport system with position retainers locking eggs in place,
a tunnel for delivering and taking away or a system of shutters,
a plurality of drive units for the shutters,
a height sensing device,
a height correction unit, for the eggs in order to compensate different heights or respectively egg sizes during the irradiation, for irradiation with same dose of electrons,
a high voltage supply unit,
a cooling system for the electron beam generator,
an ozone suction unit for the treatment area,
optionally a recontamination unit for the eggs,
the electron beam bundle from the electron beam generator for irradiation of the eggs in a treatment area,
whereby, for signaling and for operative supply, the central control unit is connected via lines to the drive units, via a line to the height sensing device, via a line to the transport system, via a line to the recontamination unit, via a line to the configurations for further processes and via a line to the height correction unit.

A second device for treatment of poultry eggs with electron beams for a sterilization of the calcareous shell, using one of the mentioned methods, at least comprises:
a transport system with at least one egg,
an electron beam source for emission of an electron beam bundle, through whose path the eggs are led in a way treated with electrons in a treatment area, whereby according to the characterizing portion of claim 6<sic. 9>
the transport system has rollers with defined spacing, on which the eggs are moved, whereby the eggs held by means of rollers are rolled through the path of the electron beam bundle in such a way that, with respect to the egg circumference, the irradiation takes place on all sides and to a large extent uniformly.

The second device for treatment of poultry eggs with electron beams for a sterilization of the calcareous shell can have furthermore the following units and lines:
a central control unit,
an electron beam generator/electron beam source,
a shielding device around the treatment unit/around the treatment area,
a transport system with rollers,
a tunnel for delivering and taking away or a system of a plurality of shutters,
a plurality of drive units for the shutters,
a height sensing device,
a height correction unit for the eggs, in order to compensate different heights or respectively egg sizes during the irradiation, for irradiation with same dose of electrons,
a high voltage supply unit,
a cooling system for the electron beam generator,
an ozone suction unit for the treatment area,
optionally a recontamination unit for the eggs,
the electron beam bundle from the electron beam generator in the treatment area of the treatment unit,
Whereby, for signaling and for operative supply, the central unit is connected via the lines to the drive units, via the line to the height sensing device, via the line to the transport system, via the line to the recontamination unit, via the line to the configurations for further processes and via the line to the height correction unit.

The central control unit is likewise connected with at least one line to
the high voltage supply unit,
the cooling system for the electron beam generator, and
the ozone suction unit for the treatment area.

A third device for treatment of poultry eggs with electron beams for a sterilization of the calcareous shell, using one of the mentioned methods comprises at least
at least one transport system with at least one egg,
at least one electron bean source for emission of an electron beam bundle through whose path the eggs are led in a way treated with electrons in a treatment area,
whereby according to the characterizing portion of claim 8<sic. 11>
provided is a combined third device, containing two first devices, constructed in the same way, whereby disposed between the two first devices is a turning device, which are connected together by means of the connecting transport system, whereby in the turning device the eggs held in a zero degree position in the first device arranged upstream of the turning device are turned at an angular degree position, e.g. in an 180 degree position, so that in each case the other opposite side of the egg receives, after the first irradiation with electrons and after passage through the turning device, while turned in the angular degree position, e.g. the 180-degree position, a second irradiation by means of the first device arranged downstream of the turning device.

The said electron baffle serves for local electron dose reduction during the electron beam treatment of hatching eggs. Further developments of the invention and further embodiments are presented in further subordinate claims.

The invention will be explained by means of embodiment examples with reference to drawings:

The disclosure is to be made with an embodiment example with eggs in the form of hatching eggs 42, 43.

DETAILED DESCRIPTION OF THE INVENTION

Figure 1:
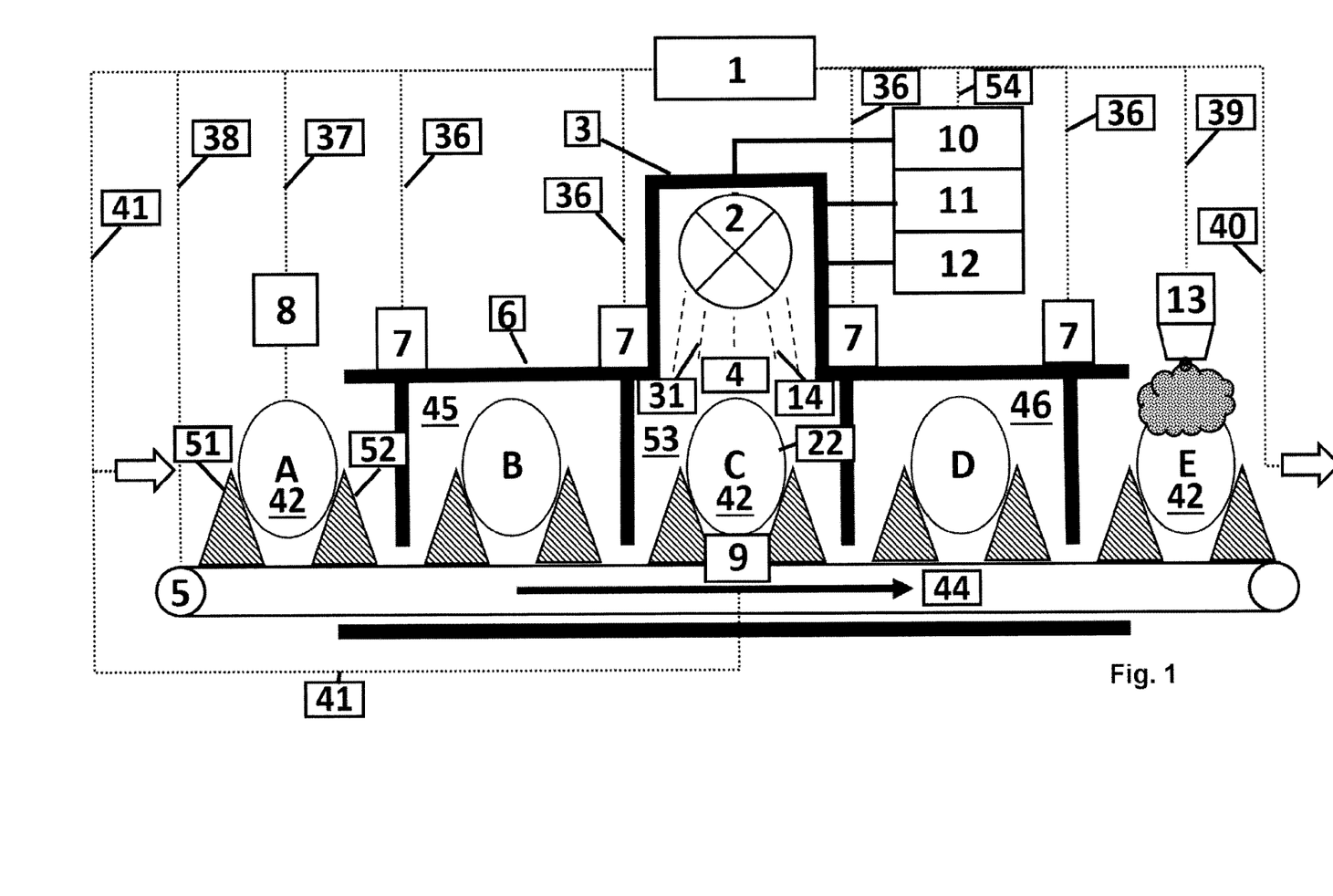
FIG. 1 shows a schematic representation of the first device according to the invention for treatment of poultry eggs with electron beams for a sterilization of the calcareous shell with eggs positioned in a fixed way in the form of hatching eggs on a transport system for carrying out a sterilization of the calcareous shell of hatching eggs in zero degree position with an optional final recontamination unit for the treated hatching eggs.

Shown in FIG. 1 is a schematic representation of a first device 20, 201 (according to FIG. 14) for treatment of eggs in the form of hatching eggs 42 with electron beams for a sterilization of the calcareous shell 22 of the hatching eggs 42, whereby a first device 20, 201 at least comprises:
 a transport system 5 with at least one hatching egg 42,
 an electron beam source 2 for emission of an electron beam bundle 14, through whose path in the treatment area 53 the hatching eggs 42 are led in a way treated with electrons 31.

According to the invention, for setting the dose 21 (according to FIG. 10) of electrons 31 hitting the calcareous shell 22 in a target dose range 18, an element 4 is disposed between the electron beam source 2 and the supported hatching egg/eggs 42, so that in a predefined target dose range 18 a reduced distribution, encompassing the hatching egg 42, of the dose 21 of the electrons 31 is achieved for irradiation of the calcareous shell 22 of the hatching eggs 42.

The element 4 for setting the dose 21 can be an electron baffle.

Figure 11:
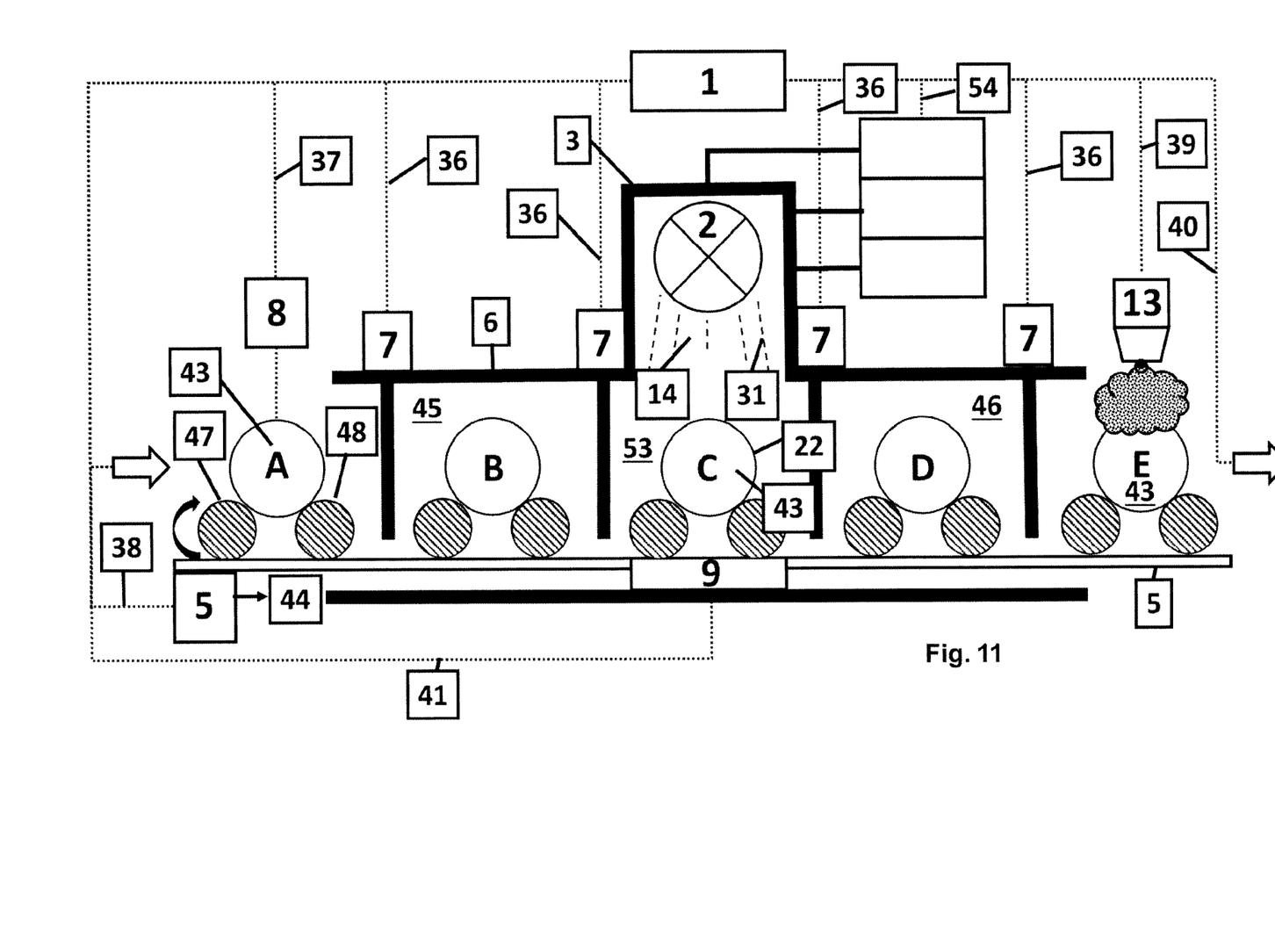
FIG. 11 shows a schematic representation of a second device according to the invention for treatment of poultry eggs with electron beams for a sterilization of the calcareous shell by means of roller-held eggs, e.g. hatching eggs, on a transport system provided with rollers with an optional final recontamination unit for the treated hatching eggs.

The first device 20, 201 (the latter according to FIG. 14) for treatment of poultry eggs 42 with electron beams 31 for a sterilization of the calcareous shell 22 thus contains in FIG. 1 the following units and lines:
 a central control unit 1,
 an electron beam generator/electron beam source 2,
 a shielding device 3 around the treatment unit 53,
 the electron baffle 4,
 a transport system 5 with position retainers 51, 52 locking eggs 42 in position,
 a tunnel 6 for delivery and taking away or a system of shutters,
 a plurality of drive units 7 for the shutters,
 a height sensing device 8,
 a height correction unit 9,
 a high voltage supply unit 10,
 a cooling system 11 for the electron beam generator 2,
 an ozone suction unit 12 for the treatment area,
 a recontamination unit 13 for the eggs 42, 43,
 an electron beam bundle 14 from the electron beam generator 2, whereby the central control unit 1 in FIG. 1 and in FIG. 11 is connected via the lines 36 to the drive units 7, via the line 37 to the height sensing device 8, via the line 38 to the transport system 5, via the line 39 to the recontamination unit 13, via the line 40 to the configurations for further processes and via the line 41 to the height correction unit 9.

Indicated in FIG. 1 and FIG. 11 are the following process steps for the treatment:
 sensing A the height of the hatching egg 42, 43,
 moving B into the shielded area through gate 45,
 treatment C with corresponding height correction unit 9,
 moving D out of the shielded area through gate 46 and
 optional recontamination E of the hatching eggs 42, 43 and transfer of the hatching egg 42, 43 for subsequent process steps.

Indicated in FIG. 1 is a schematic representation of the device 20, 201 according to the invention (according to FIG. 14) with hatching eggs 42, positioned in a fixed way, on a transport system 5 for carrying out a sterilization of the calcareous shells 22 of hatching eggs 42 in zero degree position with an optional final recontamination unit 13 for the calcareous shell-sterilized, treated hatching eggs 42.

As practice has shown, the number of viable microorganisms on or respectively in the calcareous shell 22 of hatching eggs 42, 43 can be reduced to zero with the aid of the described device 20, 201 and 30 for treatment with accelerated electrons 31. Since a disadvantage could possibly thereby result for the chicks hatching later, a well targeted and controlled recontamination of the calcareous shell 22 with microorganisms of known type and quantity, such as e.g. lactobacilli, can take place. This is possible with a recontamination unit 13, e.g. in the form of a spraying configuration as shown in FIG. 1 and FIG. 11.

Figure 2:
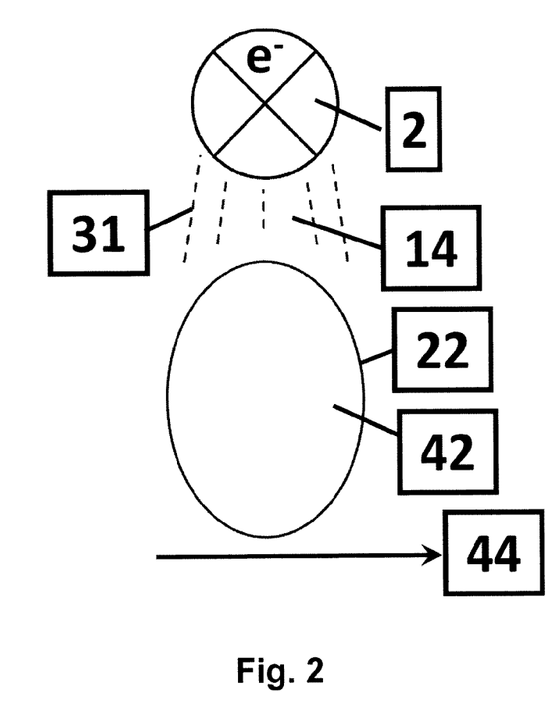
FIG. 2 shows a schematic representation of an egg, being treated with electron beams, standing in vertical pole position with predetermined direction of movement.

FIG. 2 shows a schematic representation of a hatching egg 43 being treated with an electron beam bundle 14, the egg standing in vertical pole position with a predefined direction of movement 44.

Figure 3:
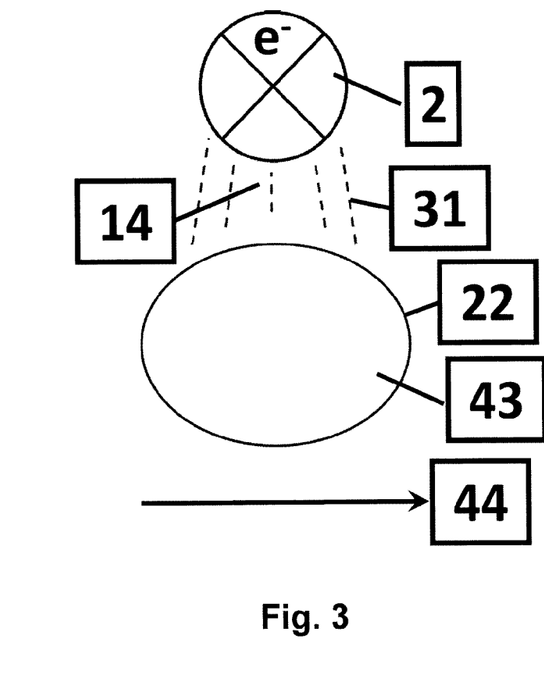
FIG. 3 shows a schematic representation of an egg, being treated with electron beams, lying in horizontal pole position with predetermined direction of movement.

FIG. 3 represents schematically a hatching egg 43 being treated with an electron beam bundle 14, which egg is indicated lying in horizontal pole position with predefined direction of movement 44.

Figure 4:
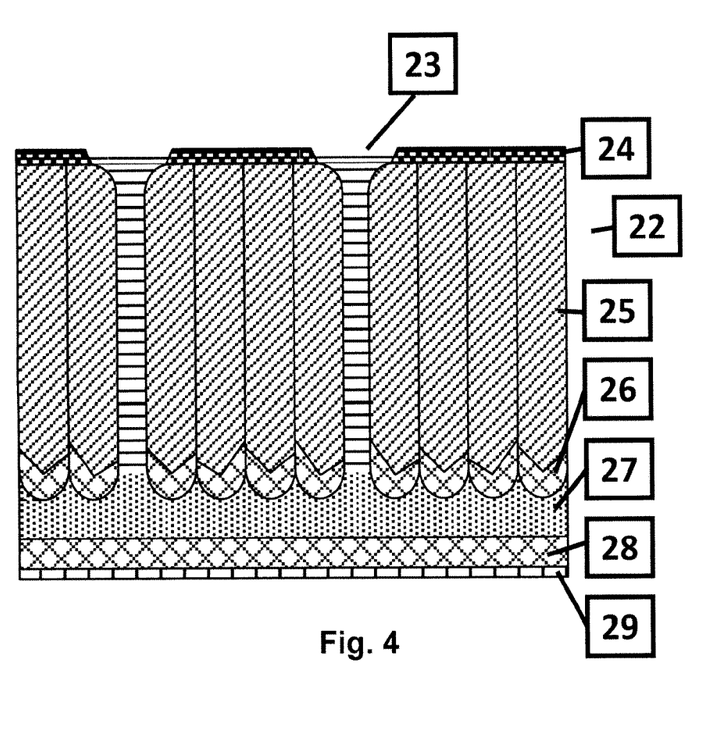
FIG. 4 shows a schematic cross section of a detail through the calcareous shell, in particular pores with pathogenic microbes located therein.

Shown in FIG. 4 is a schematic cross section of a detail through the calcareous shell 22; indicated in particular as pores 23 are possible cavities with pathogenic microbes situated therein.

The following elements belong essentially to a calcareous shell 22:
- pores 23,
- the cuticle 24,
- a palisade layer 25,
- a mammillary layer 26,
- an outer shell membrane 27,
- an inner shell membrane 28 and
- a film 29.

Figure 5:
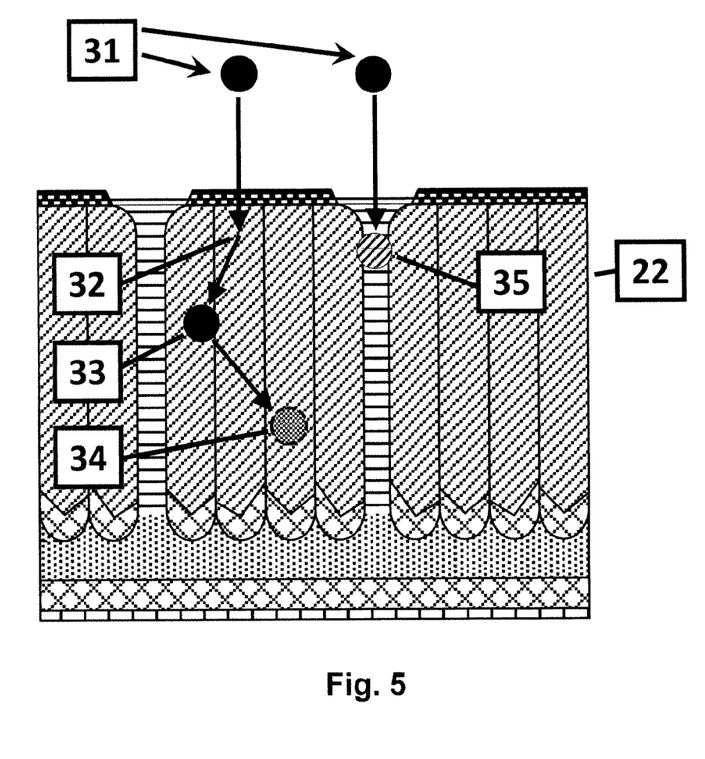
FIG. 5 shows a schematic cross section of a detail through the calcareous shell according to FIG. 4 with electrons and secondary electrons as well as the development of the ionization of oxygen to ozone within the calcareous shell.

FIG. 5 shows a schematic cross section of a detail through the calcareous shell 22 according to FIG. 4 with irradiating electrons 31 and secondary electrons 33 generated through scattering effects 32 as well as a development of the ionization 35 of oxygen into germ-killing ozone inside the calcareous shell 22, whereby the secondary electrons 33 are contained through absorption 34 in the calcareous shell 22.

Figure 6:
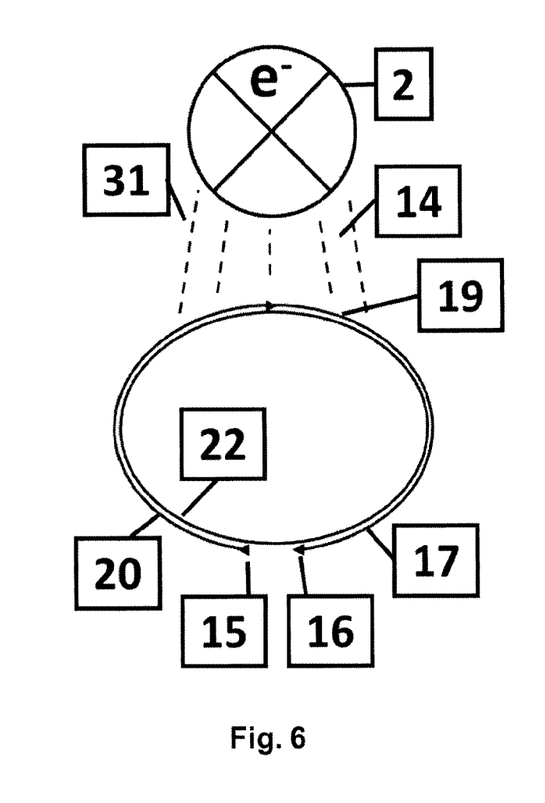
FIG. 6 shows a schematic representation of the irradiation of a hatching egg with a dose strip surrounding the egg for examination of the distribution of the electron dose around the hatching egg.

FIG. 6 shows a schematic representation of the irradiation of a hatching egg 42, 43 with a dose strip 17 surrounding the hatching egg 42, 43 for examination of the distribution of the electron dose 19, 20 around the hatching egg 42, 43.

Figure 7:
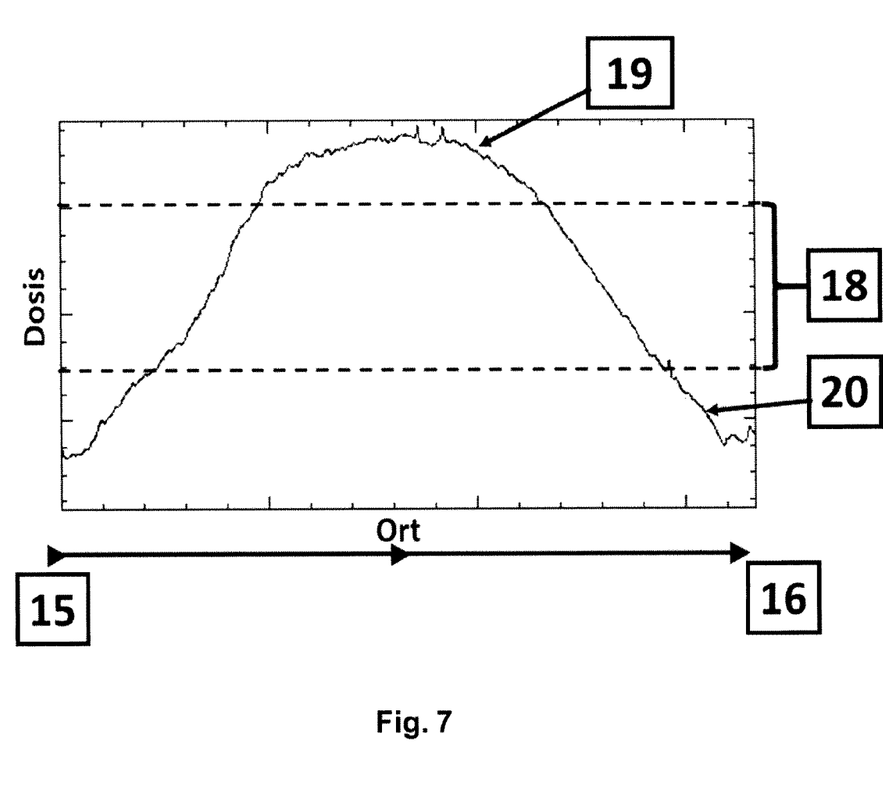
FIG. 7 shows a location/dose curve on a dose strip wrapped around the hatching egg according to a hatching egg irradiated with electrons.

For examination FIG. 7 shows a location/dose curve on a dose strip 17 wrapped around the hatching egg 42, 43 after the irradiation with electrons 31.

Figure 8:
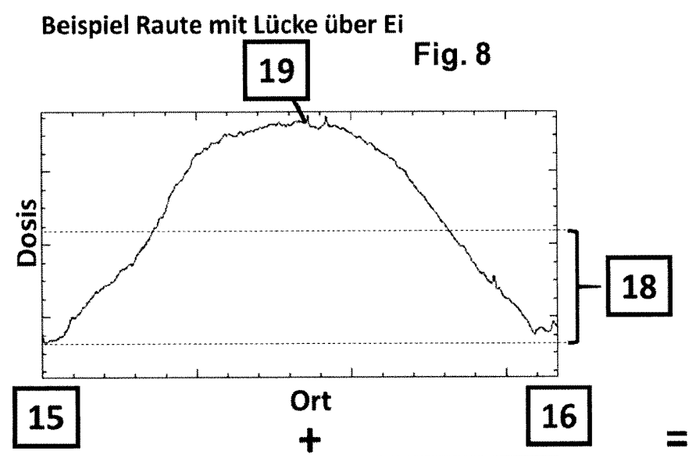
FIG. 8 shows a location/dose curve on a dose strip wrapped around the hatching egg according to FIG. 7 according to a hatching egg irradiated with electrons with increased dose rate, e.g. from 30 kGy to 45 kGy, so that the remote side of the egg lies in the target dose range.

FIG. 8 shows a location/dose curve on a dose strip wrapped around the hatching egg according to 7 according to a hatching egg irradiated with electrons with increased dose rate, e.g. from 30 kGy to 45 kGy, so that the remote side of the egg lies in the target dose range.

Essentially it should be the object of the dose strip 17 to achieve an almost uniform irradiation of the calcareous shell 22 around the egg 42, 43. The target dose range 18 is thereby far above the reduced dose 20<sic. 21> on the remote side. The target dose range 18 should be lowered through decrease of the acceleration voltage and/or of the electron current from the electron beam source. At the same time, with the element 4, the increased dose maximum on the facing side is decreased. The points 16 and 17<sic. 15> of the respective ends of the dose strip 17 also show accordingly an irradiation with electrons. A target dose range 18 is thereby reached which achieves an almost even dose over the calcareous shell 22 and cuts off the original dose maximum.

Figure 9:
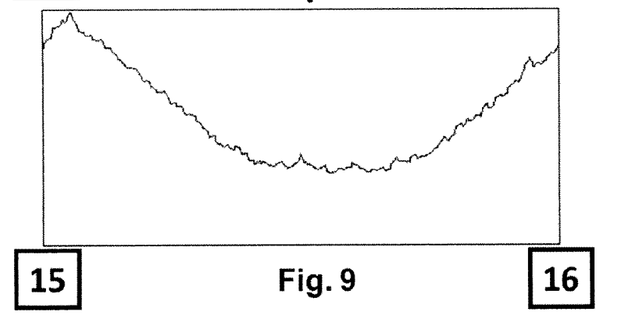
FIG. 9 shows a location/dose curve on a dose strip of a filter element penetrated by radiation with electrons for electron dose reduction in the local irradiation region of the hatching egg.

Shown in FIG. 9 is a location/dose curve on a dose strip 17 of a filter element 4 penetrated with radiation with electrons 31 for electron dose reduction in the local irradiation area of the hatching egg 42, 43, whereby with the dose course of the element the excessive dose on the facing side is weakened to the dose 21. D The element 4 for setting the dose 21 can be a steel sheet, a rod, a rhombus, a circle of aluminum. In FIG. 8 the element 4 is a rhombus with gap.

Figure 10:
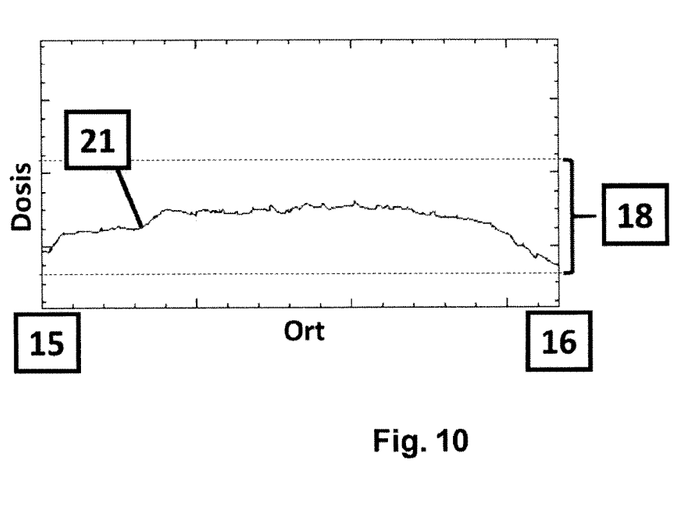
FIG. 10 shows a location/dose curve in the target dose range of a dose strip wrapped around the hatching egg using a filter element penetrated by radiation with electrons and a hatching egg located underneath.

This leveling to the dose 21 can be seen in FIG. 10.

FIG. 10 shows the result of the two dose modifications, namely, on the one hand, the dose increase on the facing side and, on the other hand, the dose decrease according to FIG. 9 through the element 4, so that the dose course 21 in FIG. 10 results, and a location/dose curve 21 located in the target dose range 18 of a dose strip 17 wrapped around the hatching egg 42, with use of a filter element penetrated by radiation with electrons 31/electron baffle 4 and a hatching egg 42 located underneath.

FIG. 11 gives a schematic representation of a second device 30 according to the invention hatching eggs 43 held by means of rollers 47, 48 on a transport system 5 equipped with rollers 47, 48 with an optional final recontamination unit 13 for the treated hatching eggs 43. The second device 30 for treatment of hatching poultry eggs with electron beams 31 for a sterilization of the calcareous shell 22 thus contains according to FIG. 11 the following units and lines, which correspond to a large extent to the elements of the first device 20:
- a central control unit 1,
- an electron beam generator/electron beam source 2,
- a shielding device 3 around the treatment unit,
- a transport system 5 with rollers 47, 48 or with a system of a plurality of roller pairs 47, 48,
- a tunnel 6 for delivery and taking away or a system of shutters,
- a plurality of drive units 7 for the shutters,
- a height sensing device 8,
- a height correction unit 9 for eggs 43 of differing size,
- a high voltage supply unit 10,
- a cooling system 11 for the electron beam generator 2,
- an ozone suction unit 12 for the treatment area,
- a recontamination unit 13 for the hatching eggs 43,
- an electron beam bundle 14 from the electron beam generator 2 for treatment of the eggs 43 in the treatment area 53, whereby the central control unit 1 in FIG. 1 and in FIG. 11 is connected via the lines 36 to the drive units 7, via the line 37 to the height sensing device 8, via the line 38 to the transport system 5, via the line 39 to the recontamination unit 13, via the line 40 to the configurations for further processes and via the line 41 to the height correction unit 9

The central control unit 1 in FIG. 1 and FIG. 11 is likewise connected at least with a line 54 or with cables to
- the high voltage supply unit 10,
- the cooling system 11 for the electron beam generator 2 and
- the ozone suction unit 12 for the treatment area 53.

Figure 12:
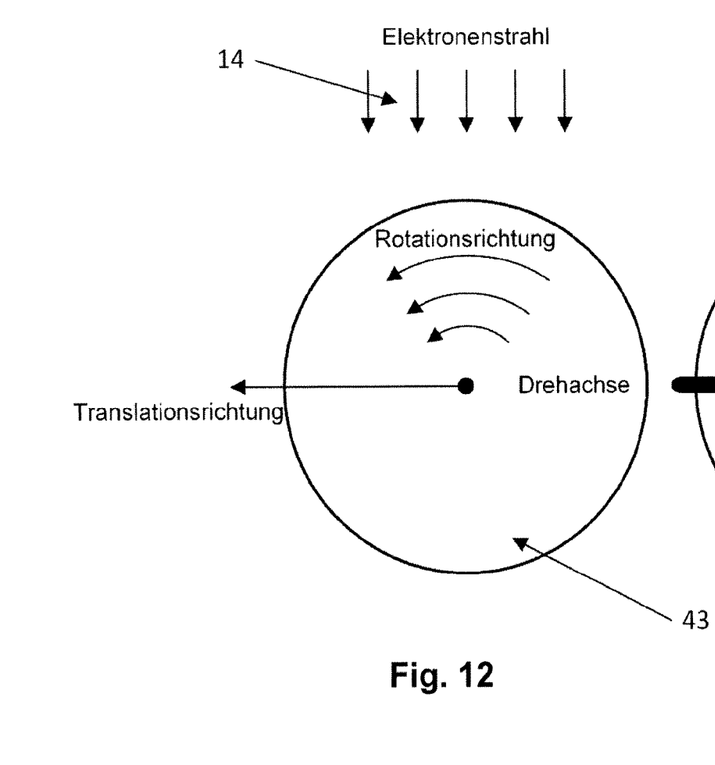
FIG. 12 shows a cross section orthogonal to the axis of the two poles of the hatching egg for rotational representation.
Figure 13:
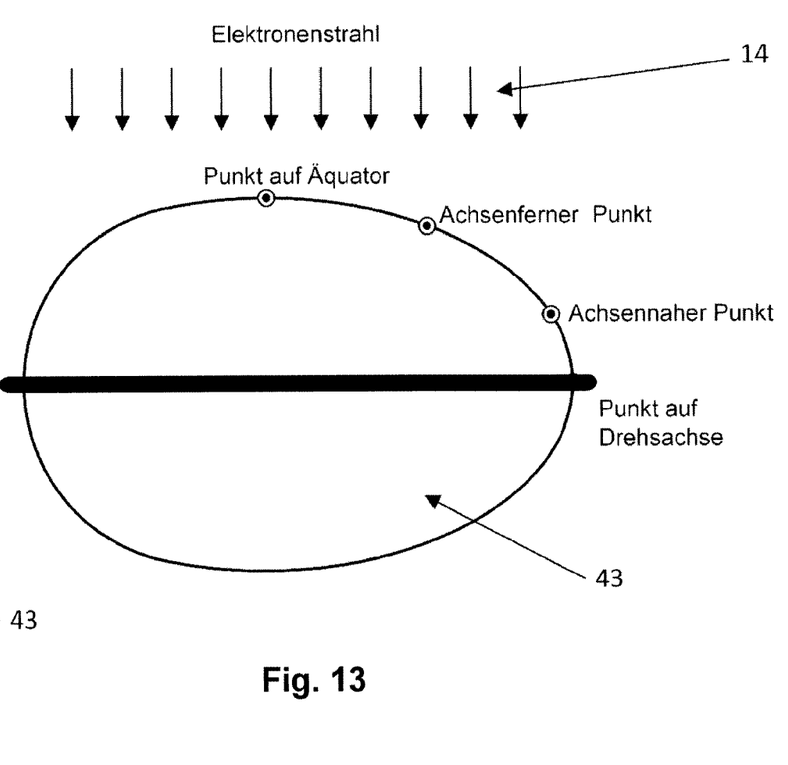
FIG. 13 shows a longitudinal section horizontal in direction to the axis of the two poles of the hatching egg with respect to the point representation and FIG. 14 shows a schematic black box representation of a third device according to the invention with held hatching eggs in zero degree position and in an angular degree position, e.g. turned 180 degree position, on a transport system with a turning device.

With the height sensing device 8 the size/the height of the eggs 42, 43 being moved past is sensed, whereby the received and forwarded signals are evaluated via the control unit 1 and are conveyed to the height correction unit 9, which adjusts in an aligning way the eggs 42, 43 coming in the meantime into the treatment area 53, so that there are no dose problems for eggs 43 of differing size, but instead there are adjusted, same irradiation doses 21. FIG. 12 shows a cross section vertical to the pole axis of the hatching egg 43, and FIG. 13 shows a longitudinal section horizontal in direction to the pole axis of the hatching egg 43. In FIG. 12 a hatching egg 43 in the form of a round body is led through an electron beam bundle 14, whereby an even irradiation on all sides of the surface is achieved. A rotation movement is thereby performed, while the hatching egg 43 is located in the beam path 14. A rotation changes the speed of points on the surface of the hatching egg 43, depending upon the spacing apart of the surface point based on the rotation. This velocity is used directly in the formula (I):

$$D = k <\blacksquare> \text{Istrahl}/V \qquad \text{(I), whereby}$$

D = a resulting dose,
k = a structurally engineered constant (also includes the spacing),
Istrahi = an electron beam current and
v = a velocity of the viewed point.

Figure 14:
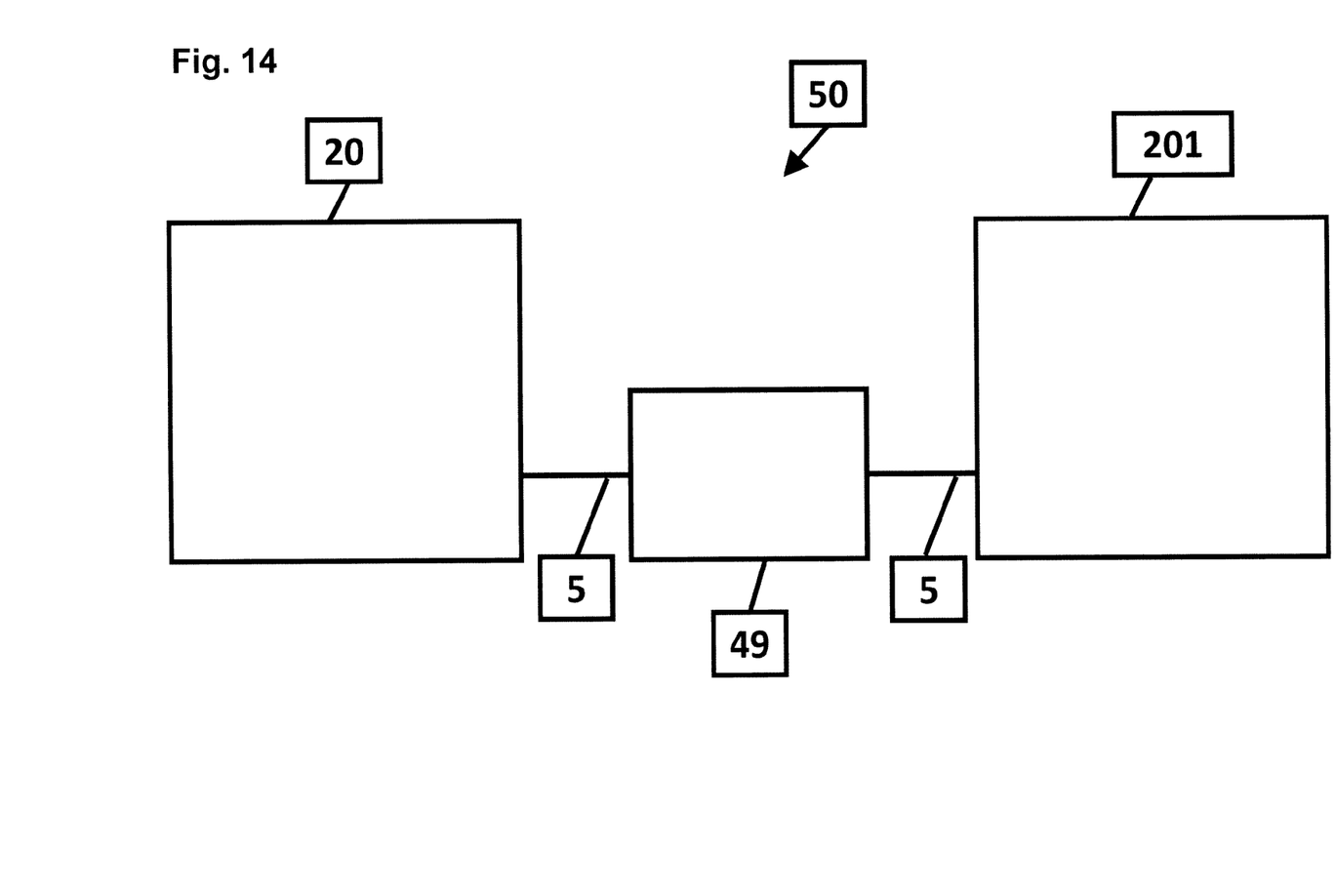

It can be concluded therefrom that a point near the axis on the surface experiences a higher dose than a point remote from the axis. The indirect proportionality D~1/v can be influenced with a translation movement of the hatching egg 43 orthogonal to the electron beam bundle 14 and orthogonal to the rotation axis. FIGS. 12 and 13 illustrate this. The representation of the three arrows of the rotational movement thereby shows that different axis spacings with same rotational angle bring with them different distances and thereby different speeds. Shown in FIG. 14 is a schematic black box representation of a combined, third device 50 according to the invention with held hatching eggs 42 in zero degree position in accordance with the first device 20 arranged upstream of a turning device and, in a pivoted e.g. 180 degree position, in accordance with a first device 201 arranged locally downstream of the turning device, with the same construction as the device 20, on a transport system 5 with turning device 49. After the first irradiation with electrons 31, during passage of the eggs in the turning device 49, the hatching eggs 42 located in zero degree position are turned in an angular degree position, e.g. 180 degree position, and subsequently on the opposite 180°-side are irradiated with electrons 31 by means of the first device 201 arranged downstream. Instead of turning the eggs 42 by an angle of 180°, the eggs 42 could be turned by a different predefined angle.

The method for treatment of hatching eggs 42, 43 with an electron beam bundle 14 for a sterilization of the calcareous shell 22 of the hatching eggs 42, 43 has the following steps:
moving at least one hatching egg 42, 43 through the beam path 14 of an electron beam source 2,
irradiating the hatching eggs 42, 43 using an electron beam bundle 14 from the electron beam source 42<sic. 2>, whereby the calcareous shell 22 is irradiated with a varying dose.

According to the invention the following steps can be carried out:
carrying out an irradiation encompassing all regions of the calcareous shell 22 of the hatching egg 42 by means of the electron beam bundle 14 whereby an element 4 is inserted into the path of the electron beam bundle 14 to distribute the irradiation over all regions of the calcareous shell 22, whereby owing to the dose being set within a predefined target dose range 18, the calcareous shell 22 is comprehensively irradiated, or
carrying out an irradiation by means of the electron beam source 2 of a rolling or rolled egg 43 in the path 14 of the electron beam bundle, whereby owing to the respective predefined rotational angle of the rolled egg 43 the calcareous shell 22 is irradiated comprehensively, or
carrying out an irradiation of the held eggs 42 at a zero degree position of the one side in a first device 20, turning of the held eggs 42 in an angular degree position turned with respect to the zero degree position, e.g. 180-degree position, by the turning device 49 and carrying out another irradiation of the other reached side of the egg 42 by means of a second device 201 which is constructed in an analogous way to the first device 20, whereby owing to the turned hatching egg 43 the calcareous shell 22 is comprehensively irradiated.

The poultry eggs 42, 43 to be treated with electron beams 31 can be eggs for human consumption, industrial eggs and preferably hatching eggs.

The invention thus also relates to a method and a device for shading (according to FIG. 8, FIG. 9, FIG. 10) or respectively for local reduction of the electron dose during the treatment of hatching eggs 42, 43 by means of accelerated electrons 31 for the purpose of sterilization (killing or respectively passivation of microorganisms such as bacteria, viruses and fungus). For this purpose, for example, the electron filter/the electron baffle 4 or respectively a barrier element of adapted geometry and adapted materials is positioned between the electron beam source 2 and the treated hatching egg 42, 43. With the aid of such an element 4, the local electron dose increase caused by the egg shape can be reduced at the areas of the treated egg 42, 43 closest to the electron beam source 2. An increase of the electron energy is thereby possible. The medium range of the accelerated electrons 31 increases, so that also egg areas situated further away can be hit by sufficiently high electron doses. As a result this leads to a reduction of the dose gradient between the calcareous shell areas 16-17 situated closest to, and furthest from, the electron beam source 2.

To prevent damaging of the hatching egg inner parts or respectively of the developing embryo, lower electron energies with lesser resultant penetration depths are used for the disinfection of the calcareous shell 22 of hatching eggs 42, 43. The accelerated electrons 31 thereby penetrate the calcareous shell 22 as a function of their energy and are scattered inelastically through scattering effects 32. Through this process a portion of the energy is deposited in the calcareous shell 22, which leads to a destruction or respectively a passivation of the microorganisms located at this place. Moreover secondary electrons 33 are generated, which can penetrate further into the calcareous shell 22 and, for their part, kill bacteria, viruses and fungus. In addition to the mentioned effects, oxygen atoms located in the microporous calcareous shell 22 become ionized and ozone is thereby generated, which penetrates, for example, through the protein coat into the nucleic acid core of viruses and damages their ribonucleic acid (RNA). These become thereby inactive or die off.

Instead of hatching eggs 42, 43, industrial eggs and eggs for human consumption can be treated according to the same method and in the same devices.

LIST OF REFERENCE NUMERALS 1 central control unit
2 electron beam generator in the treatment unit
3 shielding device around the treatment unit
4 element/electron baffle
5 transport system with position retainers/transport system with rollers
6 tunnel for delivery and taking away/system of shutters
7 drive units for the shutters
8 height sensing device
9 height correction unit
10 high voltage supply unit
11 cooling system for electron beam generator
12 ozone suction unit for treatment area
13 recontamination unit for the eggs
14 electron beam bundle
15 Beginning of the dose strip
16 End of the dose strip
17 Dose strip
18 target dose range
19 increased dose on facing side
20 first device with eggs positioned in a fixed way in zero degree position
201 first device with eggs positioned in a fixed way in angular degree position
21 measured dose in the target dose range
22 calcareous shell 23 pores
24 cuticle
25 palisade layer
26 mammillary layer
27 outer shell membrane
28 inner shell membrane
29 film
30 second device with eggs rolled in a set way
31 primary electron
32 scattering effects
33 secondary electron
34 absorption
35 ionization of oxygen and formation of ozone
36 first line
37 second line
38 third line
39 fourth line
40 fifth line
41 sixth line
42 egg/hatching egg
43 egg/hatching egg
44 direction of movement
45 gate
46 gate
47 first roller
48 second roller
49 turning device
50 third device with turning device
51 first position retainer
52 second position retainer
53 treatment area/treatment unit
54 electrical line

The invention claimed is:

1. Method for treatment of poultry eggs (42, 43) using an electron beam bundle (14) to sterilize the calcareous shell (22),
with the following steps:
moving at least one egg (42, 43) through the beam path (14) of an electron beam source (2),
irradiating the eggs (42, 43) using an electron beam bundle (14) from the electron beam source (2), whereby the calcareous shell (22) is irradiated with a varying dose,
characterized by at least one of the following steps:
carrying out an irradiation encompassing all regions of the calcareous shell (22) of the egg (42, 43) using the electron beam bundle (14) whereby an element (4) is inserted into the path of the electron beam bundle (14) to distribute the irradiation over all regions of the calcareous shell (22), whereby owing to the dose being set within a predefined target dose range (18), the calcareous shell (22) is comprehensively irradiated,
or
carrying out an irradiation by means of the electron beam source (2) of a rolling/rolled egg (43) in the path (14) of the electron beam bundle, whereby owing to the respective predefined rotational angle of the rolled egg (43) the calcareous shell (22) is irradiated comprehensively in a uniform way,
or
carrying out an irradiation by means of the electron beam source (2) of held eggs (42) in the path (14) of the electron beam bundle at a zero degree position of the one side in a device (20) arranged upstream of a turning device (49), turning of the held eggs (42) in an angular degree position turned with respect to the zero degree position by the turning device (49) and carrying out a another irradiation of another reached side of the egg (42) by means of a device (201) arranged downstream of the turning device (49) which downstream device is constructed in an analogous way to the device (20) arranged upstream, whereby owing to the turned egg (43) the calcareous shell (22) is irradiated.

2. Method according to claim 1,
wherein
the target dose range 18 is set through a variation of the acceleration voltage and/or of the electron current (31) of the electron beam source (2) via a central control unit (1).

3. Method according to claim
wherein
the following method steps for the treatment are carried out:
sensing A the height of the egg (42, 43),
moving B into the shielded area through a gate (45),
treatment C with corresponding height correction unit (9) in the case of eggs (42, 43) of differing size (42, 43),
moving D out of the shielded area through a gate (46) and
optional recontamination E of the eggs (42, 43) and transfer of the egg (42, 43) for subsequent process steps.

4. Device (20) for treatment of eggs (42) with electron beams (14) for a sterilization of the calcareous shell (22) of the eggs (42),
whereby the device (20) comprises at least:
a transport system (5) with at least one egg (42),
an electron beam source (2) for emission of an electron beam bundle (14), through whose path the eggs (42) are led in a way treated with electrons (31),
wherein
for setting the dose (21) of the electrons (31) hitting the calcareous shell (22) in a target dose range (18) an element (4) is disposed between the electron beam source (2) and the supported egg/eggs so that in a predefined target dose range (18) a reduced distribution, encompassing the egg (42), of the dose (21) of the electrons (31) is achieved for irradiation of the calcareous shell (22) of the eggs (42).

5. Device according to claim 4,
wherein
the element (4) for setting the dose (21) is an electron baffle.

6. Device according to claim 5,
wherein
the element (4) for setting the dose (21) is a steel sheet, a rod, a rhombus, a circle of aluminum or a rhombus with a gap.

7. Device according to claim 5,
wherein
at least the following units and lines are present:
the central control unit (1),
an electron beam generator/an electron beam source (2),
a shielding device (3) around the treatment unit (53),
a transport system (5) at least with position retainers (51, 52) locking eggs (42) in place,
a tunnel (6) for delivering and taking away or a system of shutters,
a plurality of drive units (7) for the shutters,
a height sensing device (8), a height correction unit (9) for alignment of eggs (42) of differing size,
a high voltage supply unit (10),
a cooling system (11) for the electron beam generator (2),
an ozone suction unit (12) for the treatment area (53),
optionally a recontamination unit (13) for the eggs (42),
the electron beam bundle (14) from the electron beam generator (2), whereby, for signaling and optionally for operative supply, the central control unit (1) is connected via the lines (36) to the drive units (7), via the line (37) to the height sensing device (8), via the line (38) to the transport system (5), via the line (39) to the recontamination unit (13), via the line (40) to the configurations for further processes and via the line (41) to the height correction unit (9).

8. Device according to claim 4,
wherein
the element (4) for setting the dose (21) is a steel sheet, a rod, a rhombus, a circle of aluminum or a rhombus with a gap.

9. Device according to claim 8,
wherein
at least the following units and lines are present:
the central control unit (1),
an electron beam generator/an electron beam source (2),
a shielding device (3) around the treatment unit (53),
a transport system (5) at least with position retainers (51, 52) locking eggs (42) in place,
a tunnel (6) for delivering and taking away or a system of shutters,
a plurality of drive units (7) for the shutters,
a height sensing device (8),
a height correction unit (9) for alignment of eggs (42) of differing size,
a high voltage supply unit (10),
a cooling system (11) for the electron beam generator (2),
an ozone suction unit (12) for the treatment area (53),
optionally a recontamination unit (13) for the eggs (42),
the electron beam bundle (14) from the electron beam generator (2), whereby, for signaling and optionally for operative supply, the central control unit (1) is connected via the lines (36) to the drive units (7), via the line (37) to the height sensing device (8), via the line (38) to the transport system (5), via the line (39) to the recontamination unit (13), via the line (40) to the configurations for further processes and via the line (41) to the height correction unit (9).

10. Device according to claim 4,
wherein
at least the following units and lines are present:
the central control unit (1),
an electron beam generator/an electron beam source (2),
a shielding device (3) around the treatment unit (53),
a transport system (5) at least with position retainers (51, 52) locking eggs (42) in place,
a tunnel (6) for delivering and taking away or a system of shutters,
a plurality of drive units (7) for the shutters,
a height sensing device (8),
a height correction unit (9) for alignment of eggs (42) of differing size,
a high voltage supply unit (10),
a cooling system (11) for the electron beam generator (2),
an ozone suction unit (12) for the treatment area (53),
optionally a recontamination unit (13) for the eggs (42),
the electron beam bundle (14) from the electron beam generator (2), whereby, for signaling and optionally for operative supply, the central control unit (1) is connected via the lines (36) to the drive units (7), via the line (37) to the height sensing device (8), via the line (38) to the transport system (5), via the line (39) to the recontamination unit (13), via the line (40) to the configurations for further processes and via the line (41) to the height correction unit (9).

11. Device (30) for treatment of eggs (43) with electron beams (31) for a sterilization of the calcareous shell (22) of the eggs (43),
whereby the device (30) comprises at least:
a transport system (5) with at least one egg (43),
an electron beam source (2) for emission of an electron beam bundle (14), through whose path the eggs (43) are led in a way treated with electrons (31),
wherein
the transport system (5) has rollers (47, 48) with defined spacing or pairs of rollers (47, 48), on which the eggs (43) are moved, whereby the eggs (43) held by means of rollers (47, 48) are rolled through the path (14) of the electron beam bundle in such a way that, with respect to the egg circumference, the irradiation with electrons (31) takes place on all sides.

12. Device according to claim 11,
wherein
at least the following units and lines are present:
a central control unit (1),
an electron beam generator/an electron beam source (2),
a shielding device (3) around the treatment unit (53),
a transport system (5) with rollers (47, 48) or a system of rollers (47,48),
a tunnel (6) for delivering and taking away or a system of a plurality of shutters,
a plurality of drive units (7) for the shutters,
a height sensing device (8),
a height correction unit (9) for alignment of eggs (43) of differing size,
a high voltage supply unit (10),
a cooling system (11) for the electron beam generator (2),
an ozone suction unit (12) for the treatment area (53),
optionally a recontamination unit (13) for the eggs (42, 43),
the electron beam bundle (14) from the electron beam generator (2), whereby, for signaling and optionally for operative supply, the central unit (1) is connected via the lines (36) to the drive units (7), via the line (37) to the height sensing device (8), via the line (38) to the transport system (5), via the line (39) to the recontamination unit (13), via the line (40) to the configurations for further processes and via the line (41) to the height correction unit (9).

13. Device (50) for treatment of eggs (42) with electron beams (31) for a sterilization of the calcareous shell (22),
whereby the device 50) at least comprises:
at least one transport system (5) with at least one egg (42),
at least one electron beam source (2) for emission of an electron beam bundle (14), through whose path the eggs (42) are led in a way treated with electrons (31), wherein
provided is a combined device (50), containing two first devices (20, 201), constructed in the same way, arranged upstream from a turning device (49), whereby disposed between the two first devices (20, 201) is a turning device (49), which is connected together by means of the connecting transport system (5), whereby in the turning device (49) the eggs (42) held in a zero degree position in the upstream-arranged device (20) are turned at an angular degree position so that in each case the other reached side of the egg (42) receives, after the first irradiation with electrons (31) and after passage through the turning device (49), while turned in the angular degree position, a second irradiation with electrons (31) by means of the first device (201) arranged downstream.

\* \* \* \* \*

UNITED STATES PATENT AND TRADEMARK OFFICE
CERTIFICATE OF CORRECTION

PATENT NO. : 11,291,191 B2
APPLICATION NO. : 16/314353
DATED : April 5, 2022
INVENTOR(S) : Meissner et al.

It is certified that error appears in the above-identified patent and that said Letters Patent is hereby corrected as shown below:

In the Drawings
FIG. 6, Reference numeral "20" should be --21--
FIG. 7, Reference numeral "20" should be --21--

In the Specification
Column 2, Lines 7-8, "claims 1 and 3, 6, 8" should be --claims 1 and 4, 11, 13--
Column 2, Line 40, "a another" should be --another--
Column 3, Lines 1-2, "claim 3<sic. 5>" should be --claim 4--
Column 3, Lines 48-49, "claim 6<sic. 9>" should be --claim 11--
Column 4, Line 27, "electron bean" should be --electron beam--
Column 4, Lines 30-31, "claim 8<sic. 11>" should be --claim 13--
Column 7, Line 24, "electron dose 19, 20" should be --electron dose 19, 21--
Column 7, Line 29, "according to 7" should be --according to FIG. 7--
Column 7, Line 36, "reduced dose 20<sic. 21>" should be --reduced dose 21--
Column 7, Line 41, "points 16 and 17<sic. 15>" should be --points 15 and 16--
Column 7, Line 52, "dose 21. D" should be --dose 21.--
Column 9, Lines 29-30, "beam source 42<sic. 2>" should be --beam source 2--
Column 10, Line 15, "shell areas 16-17" should be --shell areas 15-16--

In the Claims
Claim 1: at Column 12, Line 2, "a another" should be --an--
Claim 2: at Column 12, Line 12, "dose range 18" should be --dose range (18)--
Claim 3: at Column 12, Line 5, "Method according to claim" should be --Method according to claim 1--

Signed and Sealed this
Twenty-second Day of November, 2022

Katherine Kelly Vidal
*Director of the United States Patent and Trademark Office*